US012539387B2

(12) United States Patent
Yu et al.

(10) Patent No.: US 12,539,387 B2
(45) Date of Patent: Feb. 3, 2026

(54) POSITIVE-PRESSURE RESPIRATOR

(71) Applicant: Kaohsiung Medical University, Kaohsiung (TW)

(72) Inventors: Yu-Jhih Yu, Kaohsiung (TW); Lan-Yuen Guo, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 570 days.

(21) Appl. No.: 18/013,348

(22) PCT Filed: Jun. 30, 2021

(86) PCT No.: PCT/CN2021/103752

§ 371 (c)(1),
(2) Date: Dec. 28, 2022

(87) PCT Pub. No.: WO2022/002161

PCT Pub. Date: Jan. 6, 2022

(65) Prior Publication Data

US 2023/0263988 A1 Aug. 24, 2023

Related U.S. Application Data

(60) Provisional application No. 63/046,990, filed on Jul. 1, 2020.

(51) Int. Cl.
*A61M 16/20* (2006.01)
*A61M 16/08* (2006.01)

(52) U.S. Cl.
CPC ...... *A61M 16/201* (2014.02); *A61M 16/0875* (2013.01)

(58) Field of Classification Search
CPC .... A61F 2/18; A61F 5/08; A61F 5/56; A61M 11/006; A61M 11/06; A61M 15/0008; A61M 15/002; A61M 15/0021; A61M 15/0028; A61M 15/0031; A61M 15/0086; A61M 15/009; A61M 15/0091; A61M 15/0098; A61M 15/08; A61M 16/06; A61M 16/0605; A61M 16/0616; A61M 16/0633;
(Continued)

(56) References Cited

U.S. PATENT DOCUMENTS 6,626,179 B1 * 9/2003 Pedley .................... A61F 2/18
128/207.18
7,735,491 B2 6/2010 Doshi
(Continued)

FOREIGN PATENT DOCUMENTS

CN 101898007 A 12/2010
CN 104214384 A 12/2014

*Primary Examiner* — Annette Dixon
(74) *Attorney, Agent, or Firm* — WPAT, PC

(57) ABSTRACT

A positive airway pressure device is used to solve the problem of inconvenient use of the known positive airway pressure device and comprises: a tube including an inner end hole and an outer end hole intercommunicating with the inner end hole, with the outer end hole being smaller than the inner end hole, with the tube adapted to be inserted into a nasal cavity; and a two-way valve located in the tube, with the two-way valve moving axially between the inner end hole and the outer end hole, and with the two-way valve including a fluid passage intercommunicating with the inner end hole and the outer end hole.

10 Claims, 12 Drawing Sheets

(58) Field of Classification Search
CPC .......... A61M 16/0666; A61M 16/0672; A61M 16/0683; A61M 16/0688; A61M 16/208; A61M 2202/04; A61M 2205/0238; A61M 2210/0618
See application file for complete search history.

(56) References Cited

U.S. PATENT DOCUMENTS

| | | | | |
|---|---|---|---|---|
| 7,735,492 | B2 | 6/2010 | Doshi | |
| 7,798,148 | B2 | 9/2010 | Doshi | |
| 7,992,564 | B2 | 8/2011 | Doshi | |
| 8,215,308 | B2 | 7/2012 | Doshi | |
| 8,235,046 | B2 | 8/2012 | Doshi | |
| 8,291,909 | B2 | 10/2012 | Doshi | |
| 8,302,606 | B2 | 11/2012 | Doshi | |
| 8,365,736 | B2 | 2/2013 | Doshi | |
| 8,739,793 | B2 * | 6/2014 | Ho | A61M 16/0616 128/206.25 |
| 10,639,438 | B2 * | 5/2020 | Djupesland | A61M 11/006 |
| 2009/0194100 | A1 * | 8/2009 | Minagi | A61F 5/08 128/200.24 |
| 2011/0005520 | A1 | 1/2011 | Doshi | |
| 2018/0361108 | A1 * | 12/2018 | Nussbaum | A61M 16/208 |

* cited by examiner

POSITIVE-PRESSURE RESPIRATOR

CROSS REFERENCE TO RELATED APPLICATION

The application is a national phase entry of International Application No. PCT/CN2021/103752, filed Jun. 30, 2021, which claims the benefit of U.S. Provisional Application Ser. No. 63/046,990, filed Jul. 1, 2020, and the entire contents of which are incorporated herein by reference.

BACKGROUND OF THE INVENTION

1. Field of the Invention

The present invention relates to a breathing device and, more particularly, to a positive airway pressure device which can be completely hidden in a nasal cavity.

2. Description of the Related Art

Obstruct Sleep Apnea (OSA) is a common physical phenomenon caused by an unsmooth airway and can be rectified by a surgical or non-surgical measure. Currently, for a patient suffering from obstructive sleep apnea, the non-surgical mainstream medical therapy provides continuous positive airway pressure (CPAP) through a positive airway pressure device to expand the airway of the patient to thereby achieve a breathing-stimulating effect. This therapy can effectively improve abnormal breathing conditions including apnea, hypopnea, etc., which can effectively improve the sleep quality of the patient and, thus, reduce the possibility of cardiovascular disease and stroke.

A known positive airway pressure device includes a machine body and a ventilation hose. The machine body may include a vacuum pump therein. The volume of the machine body is about the size of a notebook computer. The ventilation hose is connected to the machine body and a breathing mask of the positive airway pressure device. In use, a patient suffering from obstructive sleep apnea wears the breathing mask during sleep. The vacuum pump in the machine body can continuously introduce positive-pressure air into the airway of the patient via the ventilation hose.

However, in the above known positive airway pressure device, since positive-pressure air must be guided into the breathing mask through the ventilation hose, to avoid the ventilation hose from being pressed by movement during sleep which causes unsmooth delivery of air or termination of supply of air, the user generally has to fix the sleeping position, which causes not only inconvenience in turning the body during sleep but also forced endurance of the feeling of an alien object connected to the body. Therefore, it is difficult for the user to enter deep sleep. Furthermore, when staying out at night, the user has to carry the whole bulky positive airway pressure device, which is extremely inconvenient in use for a person that frequently stays out at night or takes a long-distance flight.

In view of the above, improvement to the known positive airway pressure device is still necessary.

SUMMARY OF THE INVENTION

To solve the above problem, an objective of the present invention is to provide a positive airway pressure device which can be completely hidden in a nasal cavity.

Another objective of the present invention is to provide a positive airway pressure device which enhances convenience of assembly.

A further objective of the present invention is to provide a positive airway pressure device which can reduce the manufacturing costs.

Still another objective of the present invention is to provide a positive airway pressure device which can enhance the engagement stability.

The directional terms “front”, “rear”, “left”, “right”, “up (top)”, “down (bottom)”, “inner”, “outer”, “side”, and similar terms referred to herein mainly have reference to the direction of the accompanying drawings. Each of the directional and similar terms is utilized only to facilitate describing and understanding each embodiment of the present invention, rather than restricting the invention.

The term “a(n)” or “one” used for describing the number of the elements and members disclosed in the present invention is used for convenience, provides the general meaning of the scope of the present invention, and should be interpreted to include one or at least one. Furthermore, unless explicitly indicated otherwise, the concept of a single component also includes the case of plural components.

The term “engagement”, “coupling”, “assembly”, or similar terms referred to herein mainly includes separation of connected members without destroying the members after connection or inseparable connection of the members after connection. A person having ordinary skill in the art would be able to select according to desired demands in the material or assembly of the members to be connected.

A positive airway pressure device of the present invention comprises: a tube including an inner end hole and an outer end hole intercommunicating with the inner end hole, with the outer end hole being smaller than the inner end hole, with the tube adapted to be inserted into a nasal cavity; and a two-way valve located in the tube, with the two-way valve moving axially between the inner end hole and the outer end hole, and with the two-way valve including a fluid passage intercommunicating with the inner end hole and the outer end hole.

Thus, the positive airway pressure device of the present invention uses the outer end hole smaller than the inner end hole, the two-way valve moves axially between the inner end hole and the outer end hole. When the user exhales, the two-way valve moves from the inner end hole towards the outer end hole. The air current can flow from the inner end hole to pass through the fluid passage and flow towards the outer end hole. Since the outer end hole is smaller than the inner end hole, the hole diameter through which air current passes becomes smaller. As long as the user breathes normally, the positive pressure state of the airway can be achieved and extended to thereby avoid collapse of the airway. Accordingly, the related symptoms of obstructive sleep apnea can be improved. The positive airway pressure device of the present application can be completely hidden in the nasal cavity during use, which has an obvious difference in comparison with the conventional arrangement which is exposed during use. The present application can include effects of improving sleep quality, comfort use, aesthetics, and convenience.

In an example, the tube may include a tube body and a base, the tube body is coupled to the base, the inner end hole may be located in the tube body, and the outer end hole may be located in the base. Therefore, the structure is simple and easy to manufacture, which includes the effect of reducing the manufacturing costs.

In an example, the base and the tube body may together form a receiving space, the receiving space is located between the inner end hole and the outer end hole, and the two-way valve is located in the receiving space. Therefore, the structure is simple and easy to assemble, which includes the effect of assembling convenience.

In an example, the tube body may include a coupling protrusion, the base includes a recessed portion, and the coupling portion is coupled in the recessed portion. Therefore, the tube body and the base can be stably engaged with each other, which includes the effect of increasing the engagement stability.

In an example, an outer diameter of the two-way valve may be greater than a hole diameter of the inner end hole and a hole diameter of the outer end hole. Therefore, the two-way valve can be avoided from extending beyond the inner end hole or the outer end hole, which includes the effect of maintaining the function.

In an example, the two-way valve may include at least one first groove, the at least one first groove intercommunicates with the inner end hole. Therefore, the inhaled amount of the user can be increased, which includes the effect of enhancing the breathing smoothness.

In an example, the two-way valve may include a first end face and a second end face, the first groove may be located on the first end face, and the first groove may extend along an outer wall of the two-way valve in a direction towards the second end face. Therefore, the structure is simple and easy to manufacture, which includes the effect of reducing the manufacturing costs.

In an example, the tube may include at least one second groove, and the at least one second groove intercommunicates with the inner end hole. Therefore, the inhaled amount of the user can be increased, which includes the effect of enhancing the breathing smoothness.

In an example, the positive airway pressure device of the present invention may further comprise a film, and the film is coupled to an outer peripheral wall of the tube. Therefore, the film can be used to absorb mucus or tissue fluid, which includes the effect of increasing comfort during use.

In an example, the film may be made of polyurethane material. Therefore, a better absorption effect of the tissue fluid can be provided, which includes the effect of improving the product quality.

DETAILED DESCRIPTION OF THE INVENTION

Figure 1:
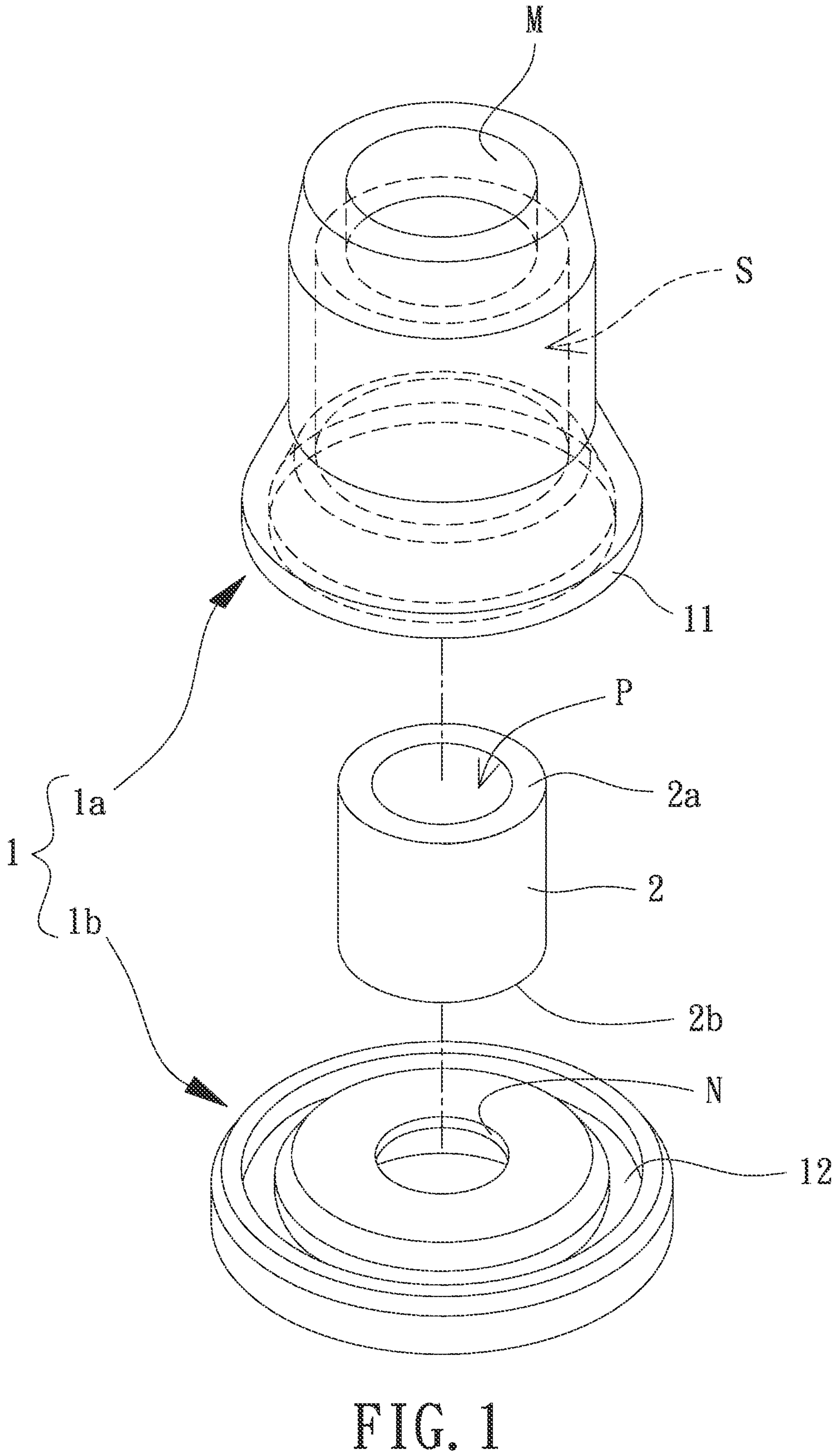
FIG. 1 is an exploded, perspective view of a first embodiment of the present invention.

In order to make the above and other objectives, features, and advantages of the present invention clearer and easier to understand, preferred embodiments of the present invention will be described hereinafter in connection with the accompanying drawings as follows:

Please refer to FIG. 1 which shows a first embodiment of a positive airway pressure device of the present invention comprising a tube 1 and a two-way valve 2. The two-way valve 2 is located in the tube 1.

Figure 2:
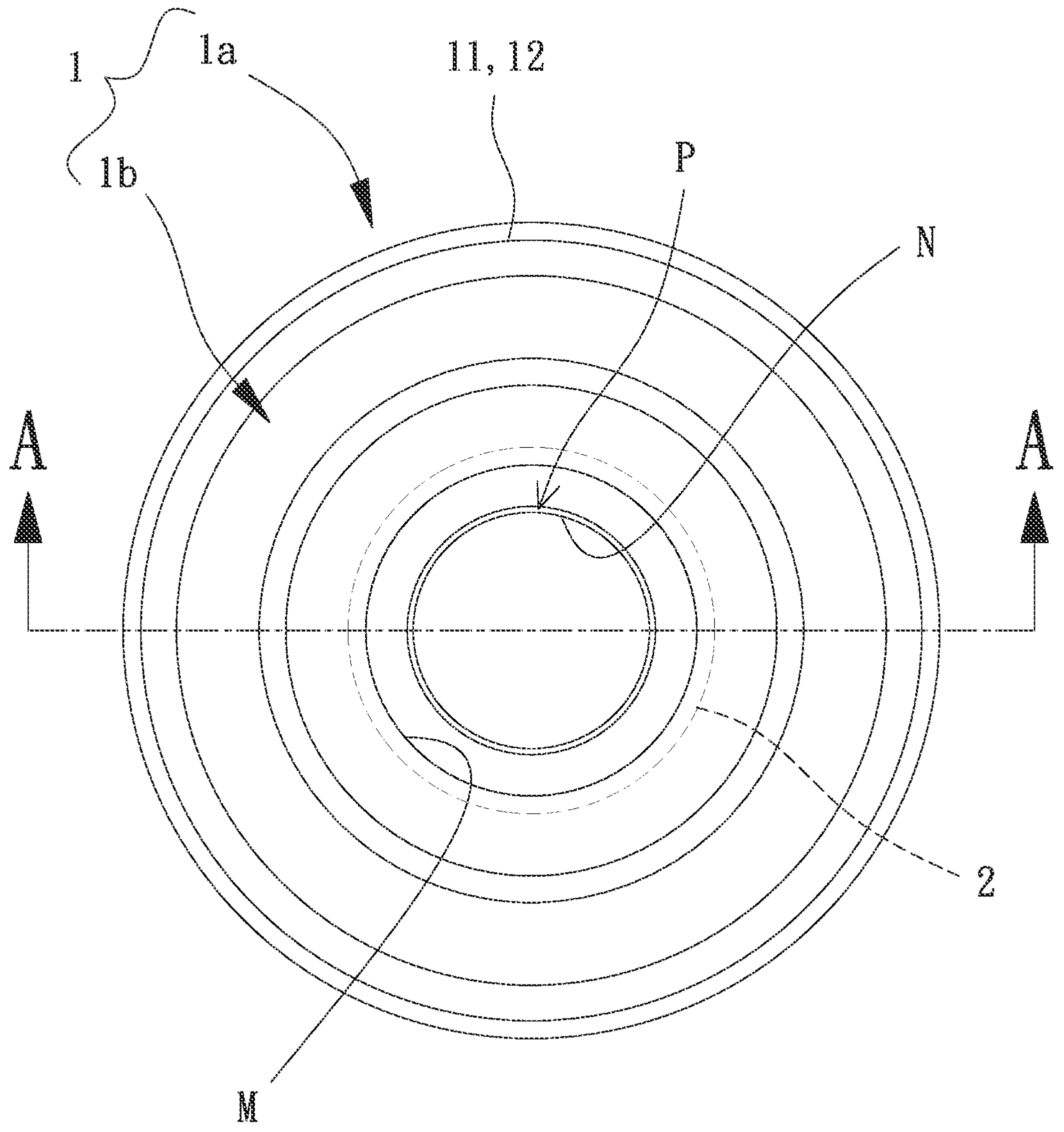
FIG. 2 is a top view of the first embodiment of the present invention after assembly.

Please refer to FIG. 1 and FIG. 2. The tube 1 may be adapted for insertion into a nasal cavity of a user. The tube 1 includes an inner end hole M and an outer end hole N intercommunicating with the inner end hole M. The outer end hole N is smaller than the inner end hole M. The inner end hole M may be closer to a deeper portion in the nasal cavity than the outer end hole N. The outline and the configuration of the tube 1 are not limited in the present invention as long as the outer end hole N is smaller than the inner end hole M. In this embodiment, the tube 1 may include a tube body 1*a* and a base 1*b*. The tube body 1*a* is coupled to the base 1*b*. The inner end hole M may be located in the tube body 1*a*. The outer end hole N may be located in the base 1*b*. The base 1*b* and the tube body 1*a* may together form a receiving space S. The receiving space S may be located between the inner end hole M and the outer end hole N.

The tube body 1*a* and the base 1*b* can be engaged with each other by snap-coupling, insertion, or threading connection. The present invention is not limited in this regard and is also not restricted to the accompanying drawings disclosed by this embodiment. In this embodiment, the tube body 1*a* may include a coupling protrusion 11. The coupling protrusion 11 extends towards the base 1*a*. The base 1*b* may include a recessed portion 12. The coupling protrusion 11 may be snap-coupled in the recessed portion 12, such that the tube body 1*a* and the base 1*b* can be stably engaged with each other.

Figure 3:
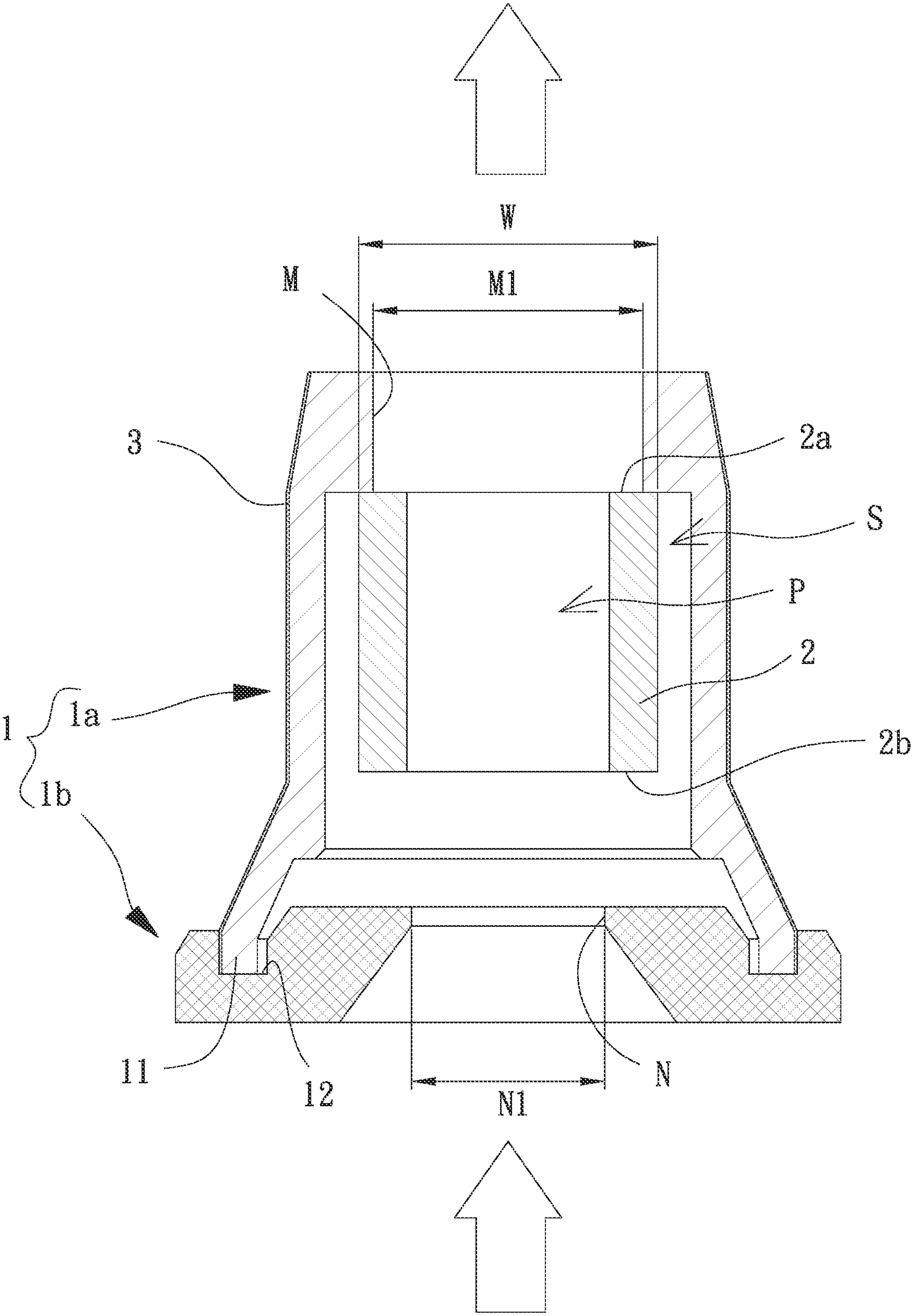
FIG. 3 is a cross sectional view taken along section line A-A of FIG. 2.

Please refer to FIG. 1 and FIG. 3. The two-way valve 2 is located in the receiving space S of the tube 1. The two-way valve 2 may include a first end face 2*a* and a second end face 2*b*. The first end face 2*a* is adjacent to the inner end hole M. The second end face 2*b* is adjacent to the outer end hole N. The two-way valve 2 moves axially between the inner end hole M and the outer end hole N. The two-way valve 2 includes a fluid passage P intercommunicating with the inner end hole M and the outer end hole N. Furthermore, an outer diameter W of the two-way valve 2 is preferably greater than a hole diameter M1 of the inner end hole M and a hole diameter N1 of the outer end hole N, avoiding the two-way valve 2 from extending beyond the inner end hole M or extending beyond the outer end hole N.

The positive airway pressure device of the present invention may further comprise a film 3. The film 3 is coupled to an outer peripheral wall of the tube 1. Therefore, when the tube 1 is located in the nasal cavity, the film 3 can be used to absorb mucus or tissue fluid, which can increase comfort during use. The film 3 may be selected to be preferably made of polyurethane material.

Figure 4:
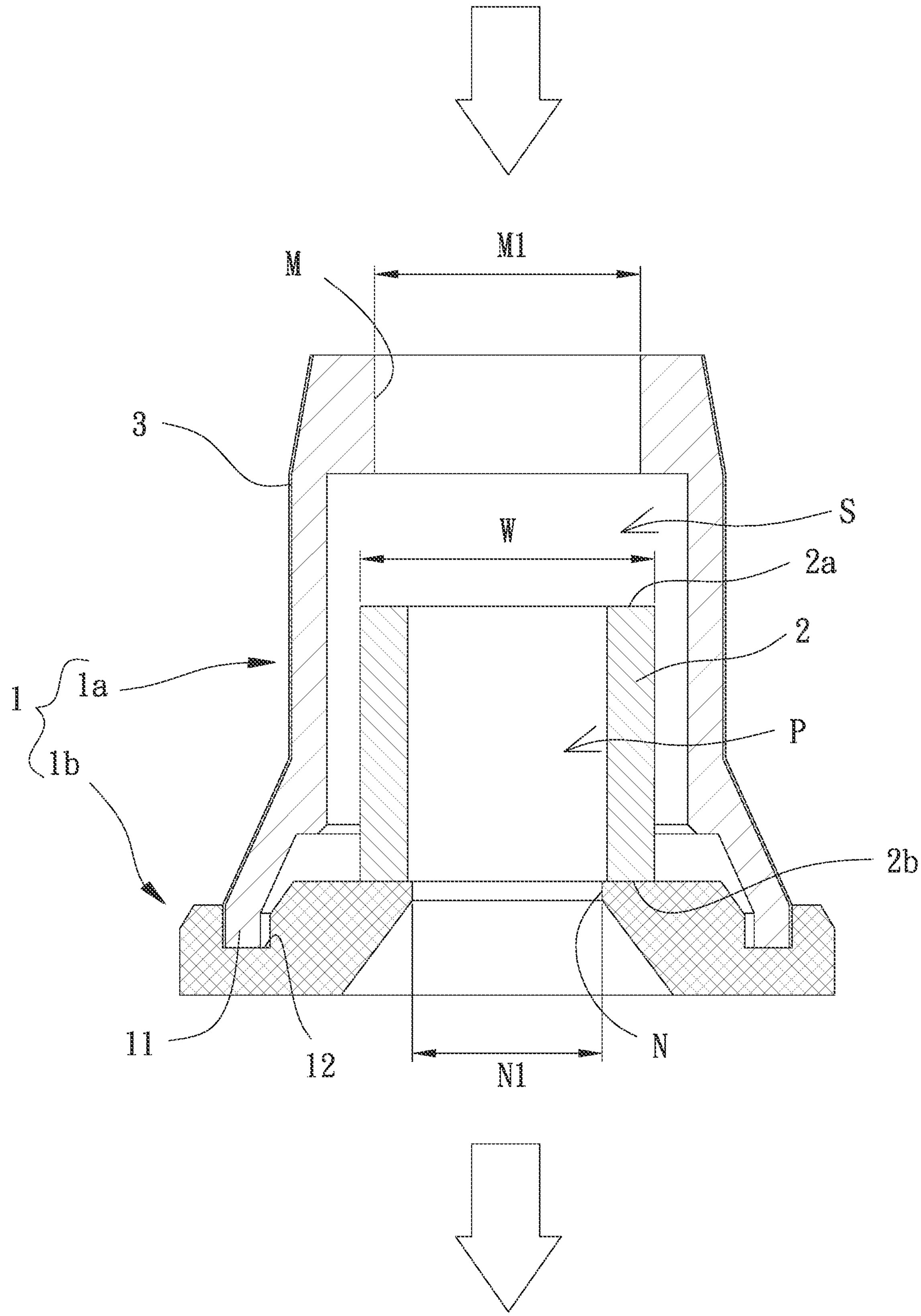
FIG. 4 is a view similar to FIG. 3, illustrating use thereof during exhalation.

Please refer to FIG. 3 and FIG. 4. When the user inhales, air current pushes the two-way valve 2 to move the two-way valve 2 from the outer end hole N towards the inner end hole M. The air current can flow from the outer end hole N to pass through the fluid passage P and flow towards the inner end hole M. Since the inner end hole M is larger than the outer end hole N, the air current can smoothly flow out of the inner end hole M without affecting the inhaling function. When the user exhales, air current pushes the two-way valve 2 to move the two-way valve 2 from the inner end hole M towards the outer end hole N. The air current can flow from the inner end hole M to pass through the fluid passage P and flow towards the outer end hole N. Since the outer end hole N is smaller than the inner end hole M, the hole diameter through which the air current passes becomes smaller. According to the pursed-lip breathing technique (the principle of the diameter of the inhaling tube greater than the diameter of the exhaling tube), as long as the user breathes normally, a positive pressure state of the airway can be achieved and extended, which can have the function of positive end-expiratory pressure (PEEP). Thus, the effect of positive end-expiratory pressure can be provided to thereby avoid collapse of the airway. Accordingly, the related symptoms of obstructive sleep apnea can be improved.

Figure 5:
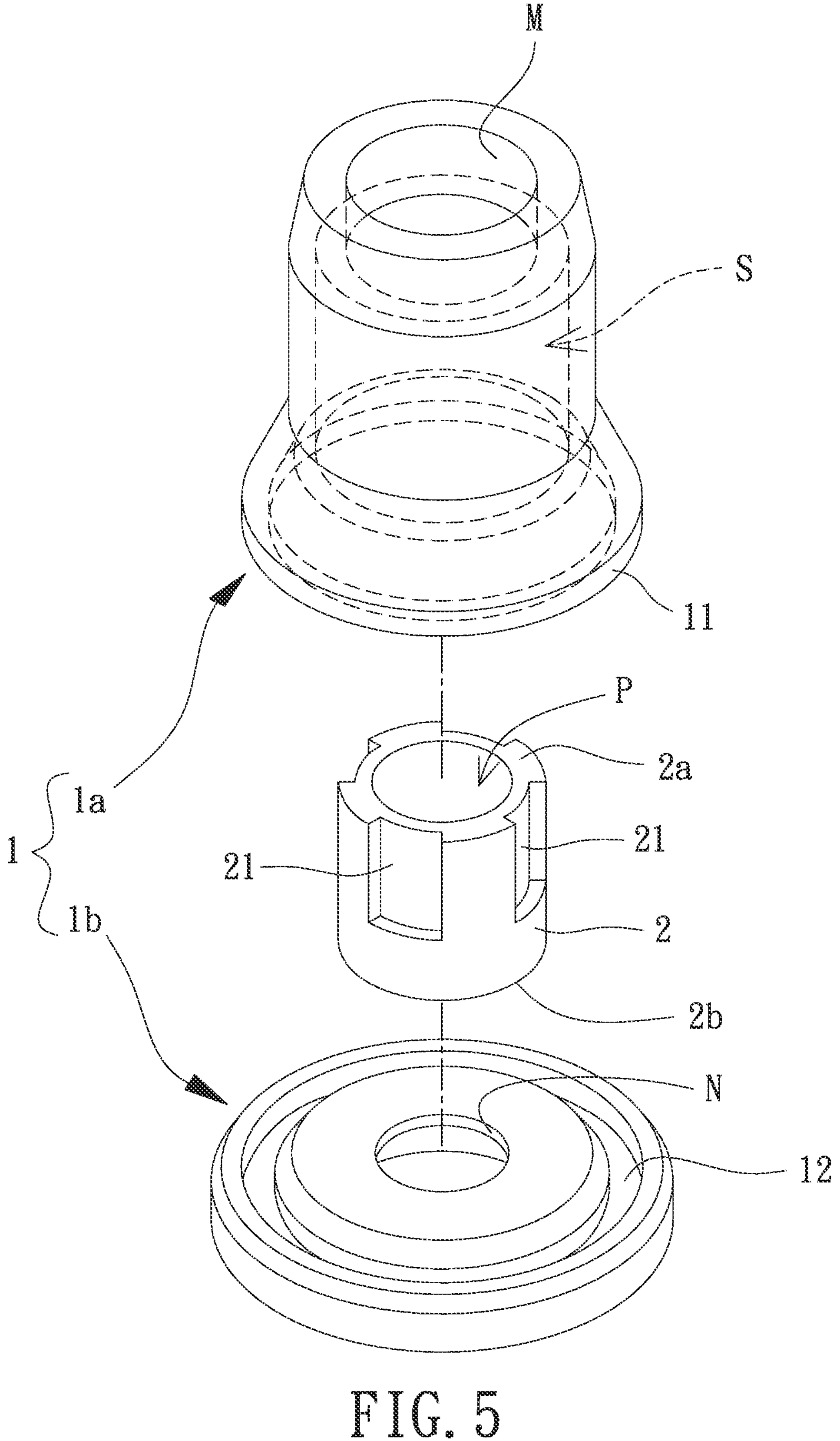
FIG. 5 is an exploded, perspective view of a second embodiment of the present invention.
Figure 6:
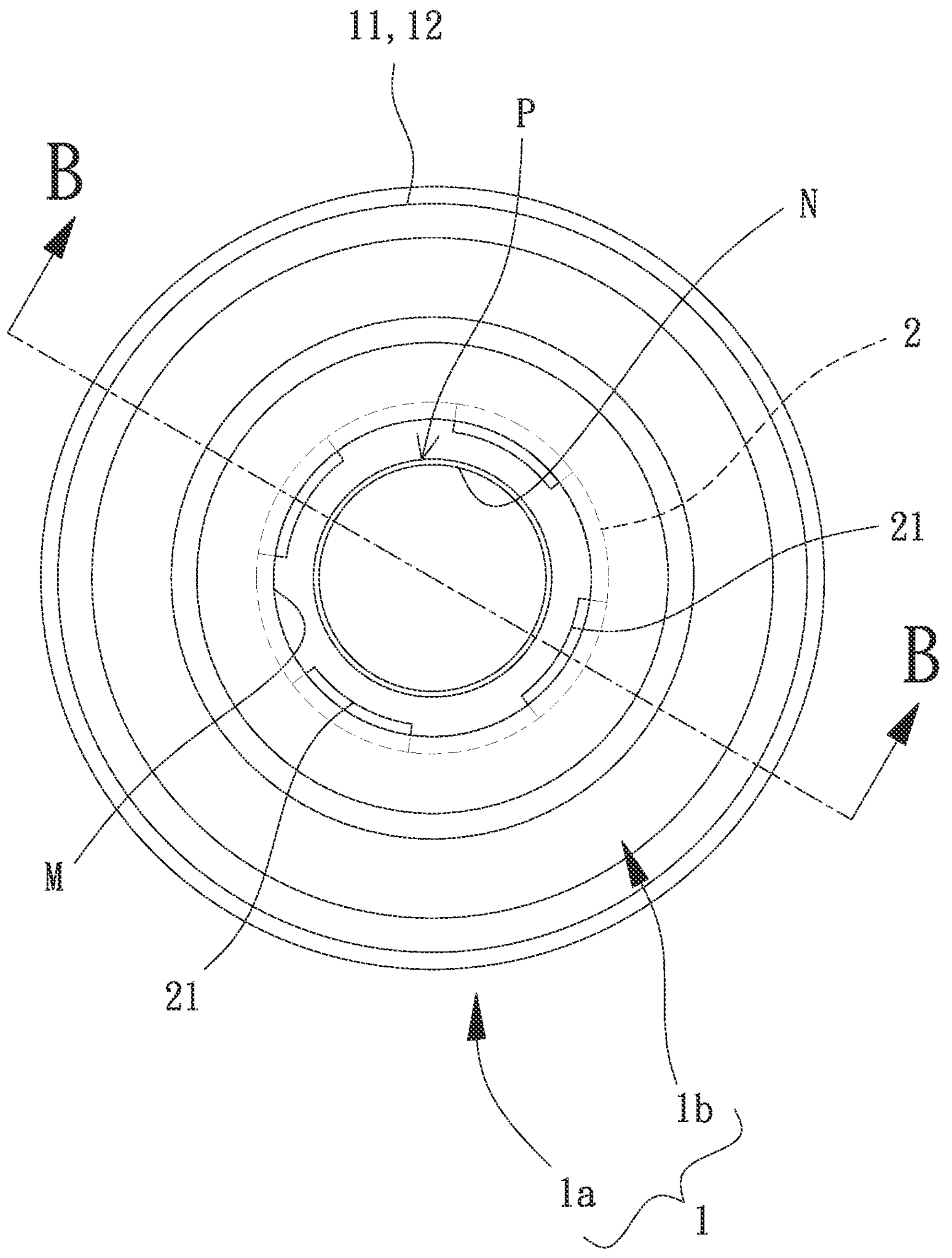
FIG. 6 is a top view of the second embodiment of the present invention after assembly.

Please refer to FIG. 5 and FIG. 6 which show a second embodiment of the positive airway pressure device of the present invention. The two-way valve 2 may include at least one first groove 21. The at least one first groove 21 intercommunicates with the inner end hole M. In this embodiment, there are plural first grooves 21. The plural first grooves 21 are located on the first end face 2*a*. Furthermore, the plural first grooves 21 extend along an outer wall of the two-way valve 2 in a direction towards the second end face 2*b*.

Figure 7:
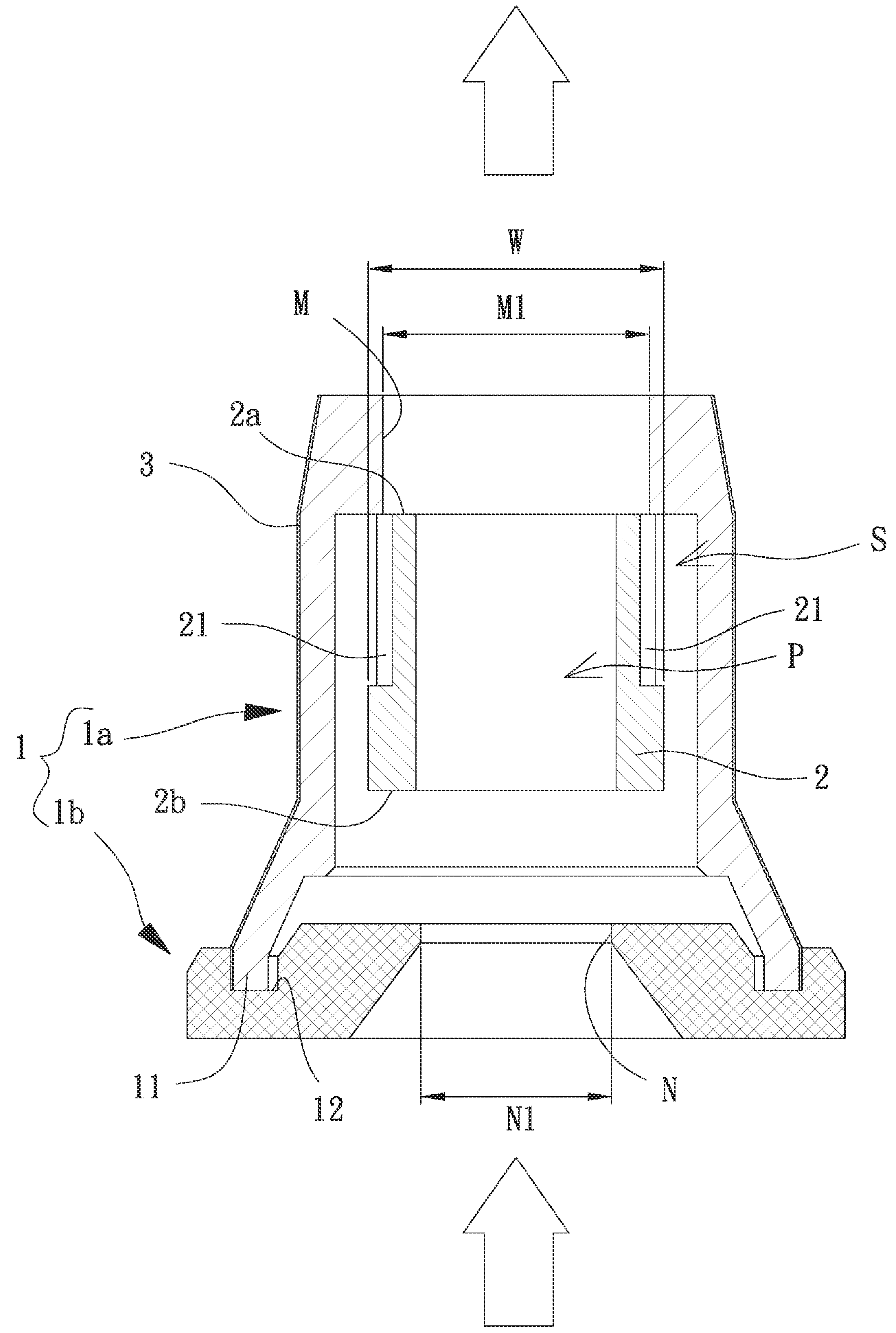
FIG. 7 is a cross sectional view taken along section line B-B of FIG. 6.
Figure 8:
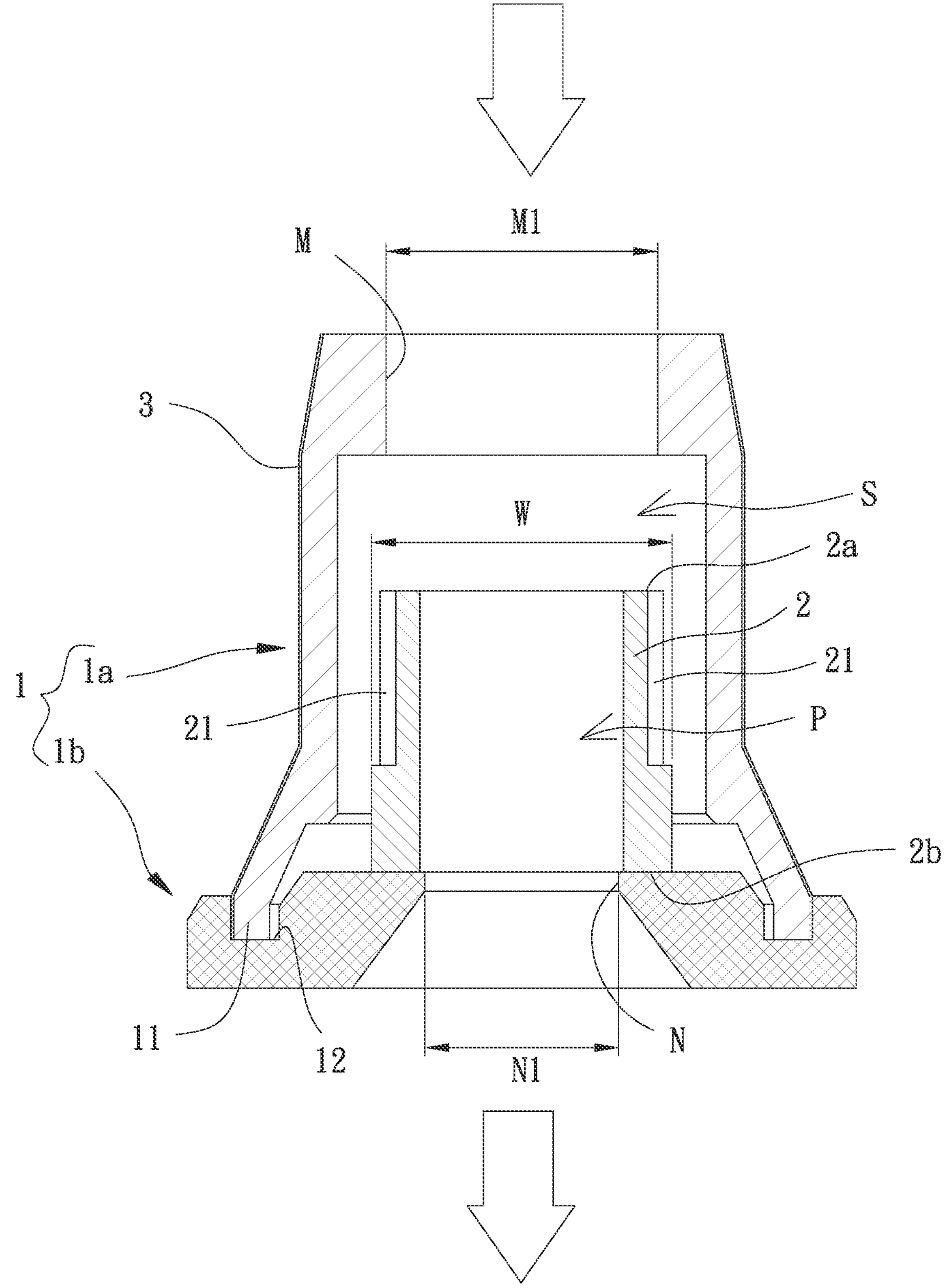
FIG. 8 is a view similar to FIG. 7, illustrating use thereof during exhalation.

Please refer to FIG. 7 and FIG. 8. Therefore, when the user inhales, the two-way valve 2 moves from the outer end hole N towards the inner end hole M. Aside from flowing from the outer end hole N to pass through the fluid passage P and flow towards the inner end hole M, the air current can also flow from the outer end hole N to pass through the plural first grooves 21 and flow towards the inner end hole M, which can increase the inhaled amount of the user to enhance the breathing smoothness. When the user exhales, the two-way valve 2 moves from the inner end hole M towards the outer end hole N. The air current can flow from the inner end hole M to pass through the fluid passage P and flow towards the outer end hole N. Since the outer end hole N is smaller than the inner end hole M, the hole diameter through which air current passes becomes smaller. Thus, the effect of positive end-expiratory pressure can be provided to thereby avoid collapse of airway. Accordingly, the related symptoms of obstructive sleep apnea can be improved.

Figure 9:
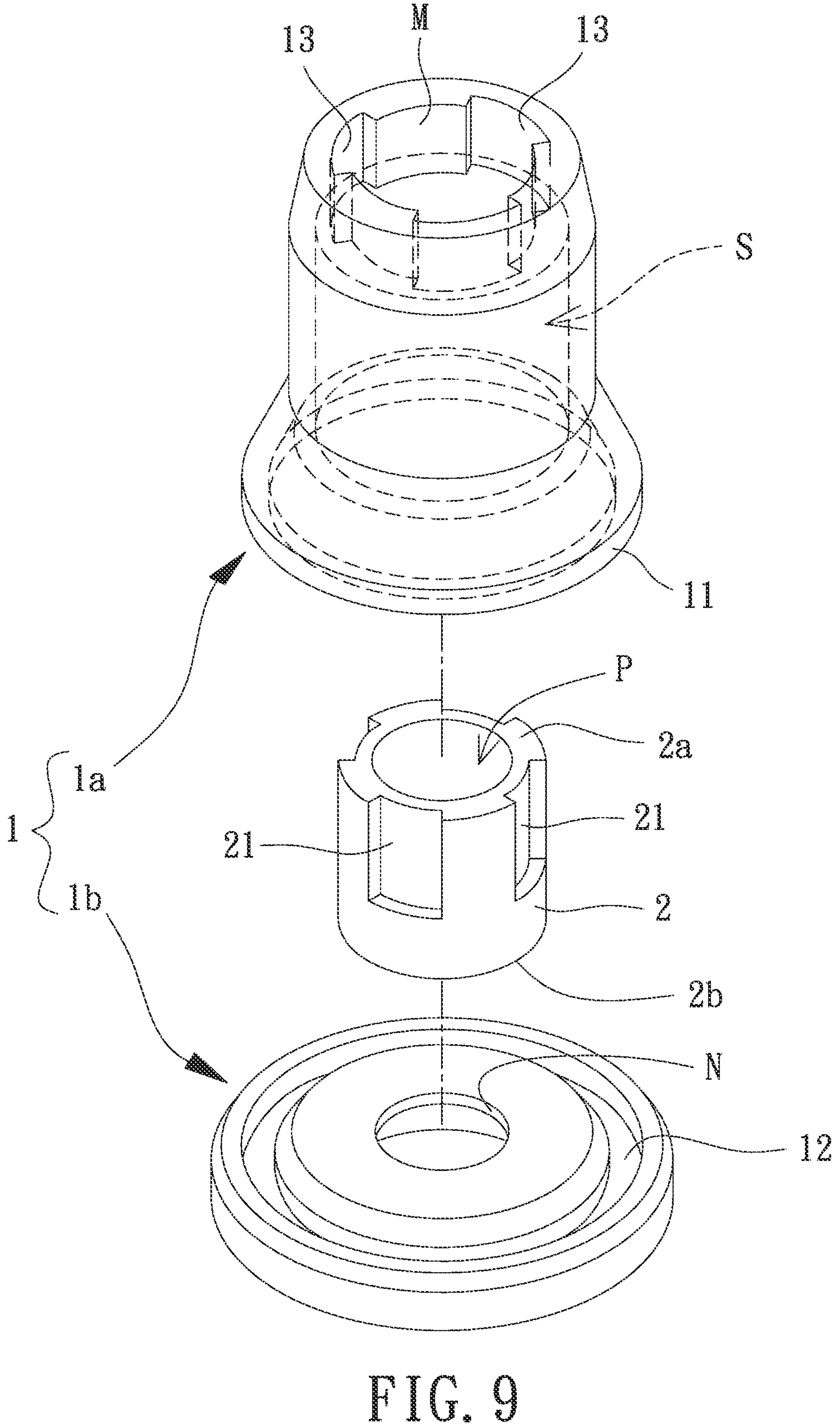
FIG. 9 is an exploded, perspective view of a third embodiment of the present invention.
Figure 10:
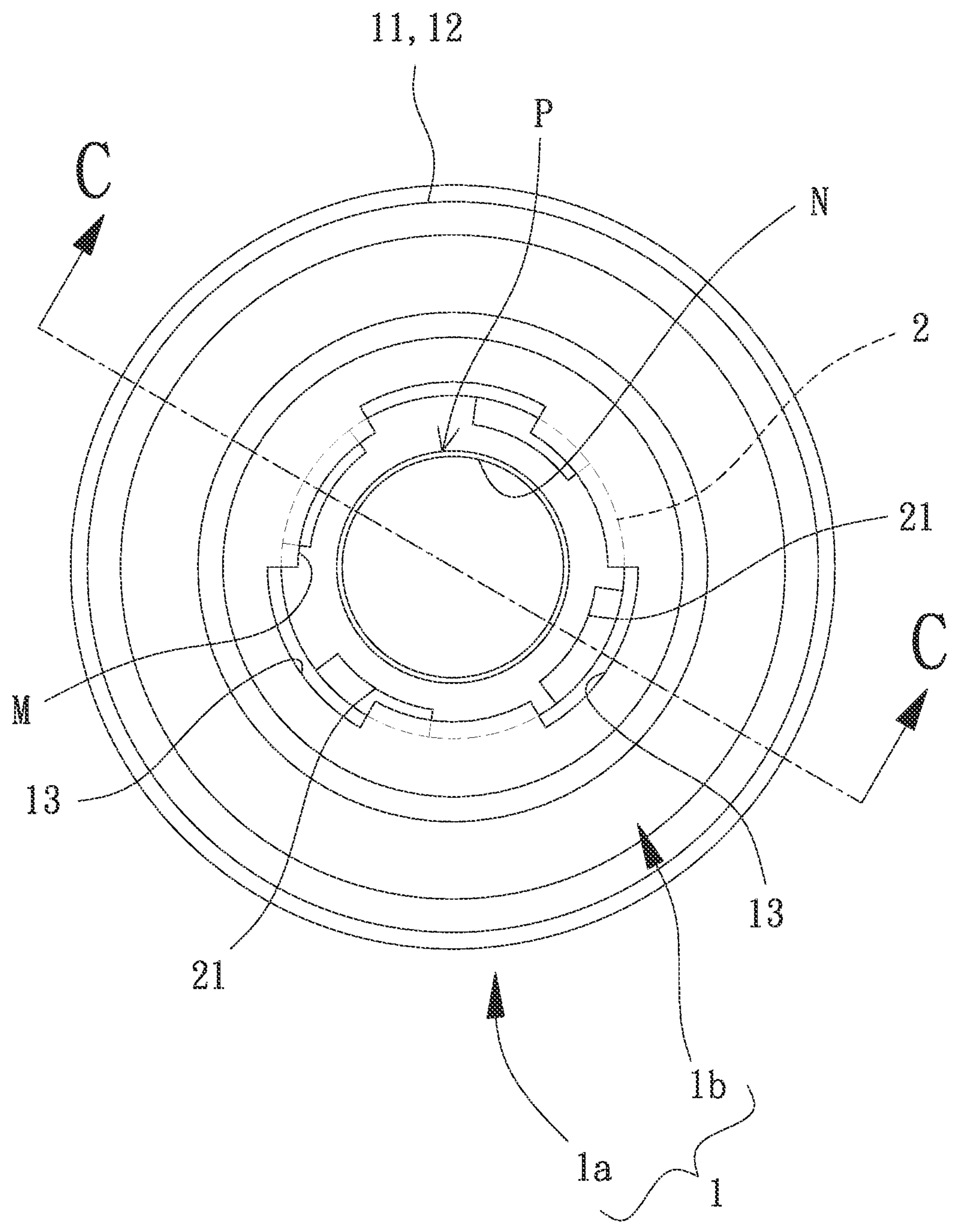
FIG. 10 is a top view of the third embodiment of the present invention after assembly.

Please refer to FIG. 9 and FIG. 10 which show a third embodiment of the positive airway pressure device of the present invention. The tube 1 may include at least one second groove 13. The at least one second groove 13 intercommunicates with the inner end hole M. In this embodiment, there are plural second grooves 13. The plural second grooves 13 are recessed in an inner wall of the inner end hole M, such that the plural second grooves 13 can intercommunicate with the inner end hole M and the plural first grooves 21.

Figure 11:
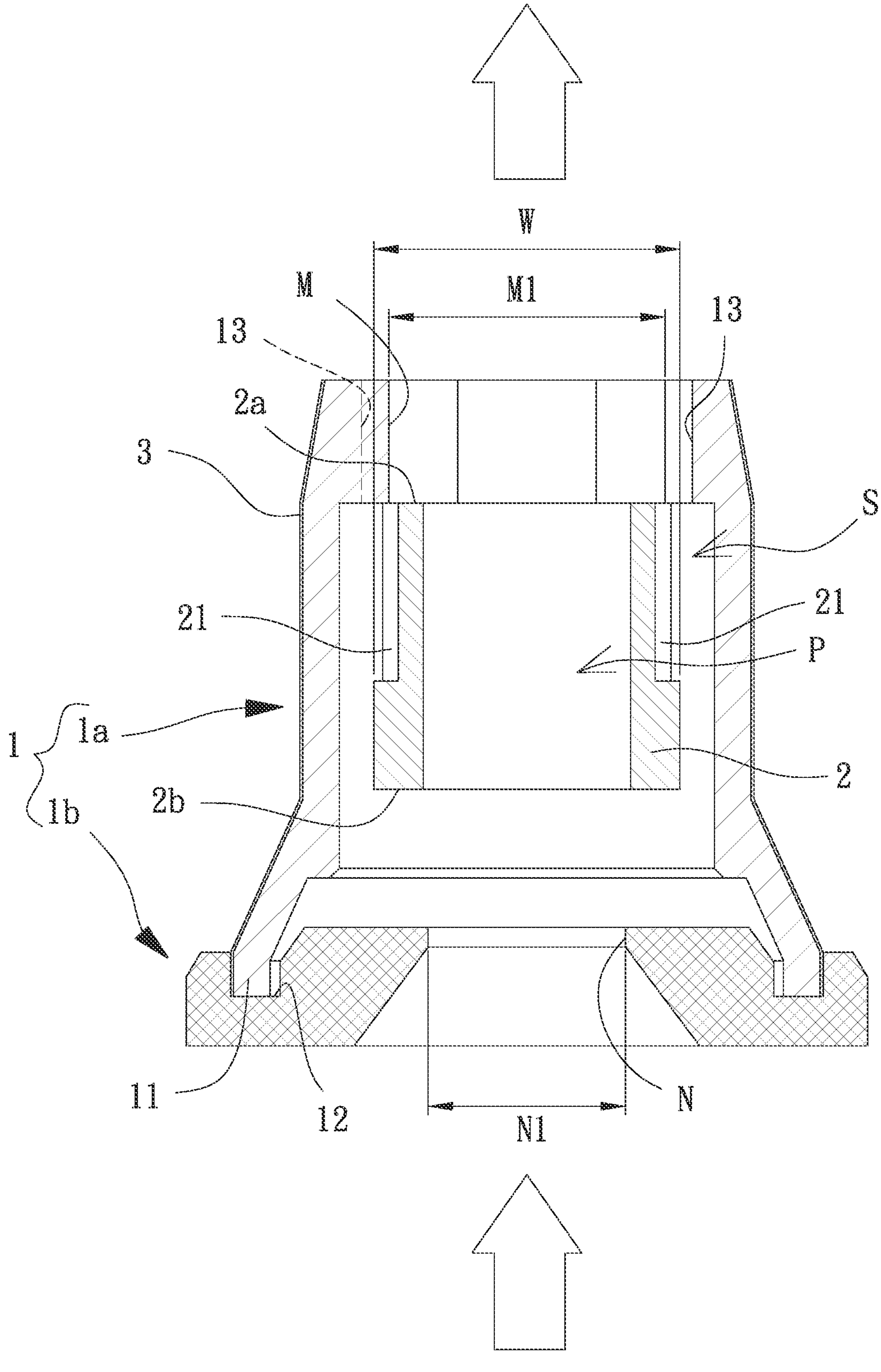
FIG. 11 is a cross sectional view taken along section line C-C of FIG. 10.
Figure 12:
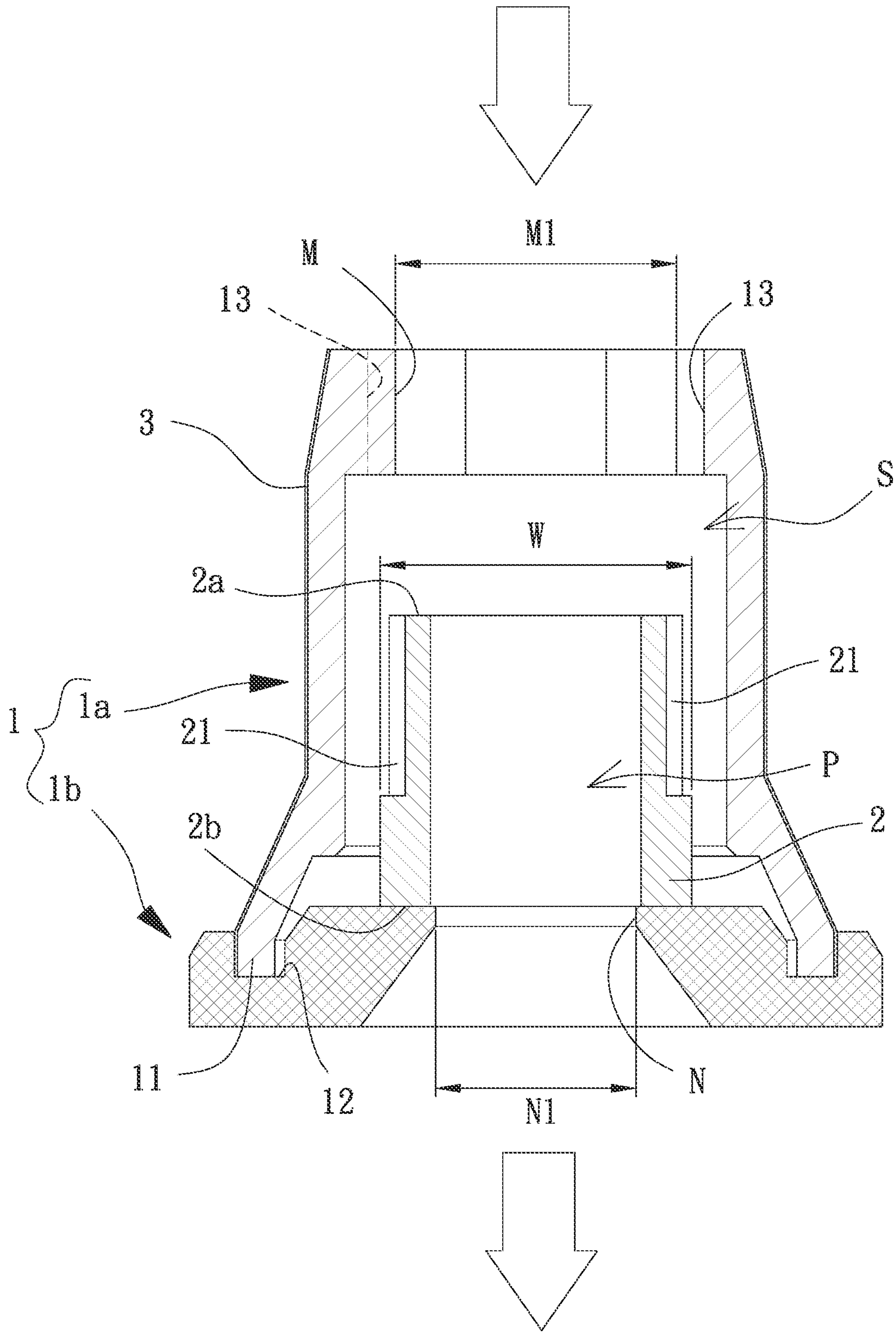
FIG. 12 is a view similar to FIG. 11, illustrating use thereof during exhalation.

Please refer to FIG. 11 and FIG. 12. When the user inhales, the two-way valve 2 moves from the outer end hole N towards the inner end hole M. Aside from flowing from the outer end hole N to pass through the fluid passage P and flow towards the inner end hole M, the air current can also flow from the outer end hole N to pass through the plural first grooves 21 and flow towards the inner end hole M and the plural second grooves 13, which can increase the inhaled amount of the user to enhance the breathing smoothness. When the user exhales, the two-way valve 2 moves from the inner end hole M towards the outer end hole N. The air current can flow from the inner end hole M to pass through the fluid passage P and flow towards the outer end hole N. Since the outer end hole N is smaller than the inner end hole M, the hole diameter through which air current passes becomes smaller. Thus, the effect of positive end-expiratory pressure can be provided to thereby avoid collapse of the airway. Accordingly, the related symptoms of obstructive sleep apnea can be improved.

In view of the foregoing, the positive airway pressure device of the present invention uses the outer end hole smaller than the inner end hole, the two-way valve moves axially between the inner end hole and the outer end hole. When the user exhales, the two-way valve moves from the inner end hole towards the outer end hole. The air current can flow from the inner end hole to pass through the fluid passage and flow towards the outer end hole. Since the outer end hole is smaller than the inner end hole, the hole diameter through which air current passes becomes smaller. Thus, the positive pressure state of the airway can be achieved and extended to thereby avoid collapse of the airway. Accordingly, the related symptoms of obstructive sleep apnea can be improved. The positive airway pressure device of the present application can be completely hidden in the nasal cavity during use, which has an obvious difference in comparison with the conventional arrangement which is exposed during use. The present application can include effects of improving sleep quality, comfort use, aesthetics, and convenience.

Although the present invention has been described with respect to the above preferred embodiments, these embodiments are not intended to restrict the present invention. Various changes and modifications on the above embodiments made by any person skilled in the art without departing from the spirit and scope of the present invention are still within the technical category protected by the present invention. Accordingly, the protection scope of the present invention is to be indicated by the claims.

What is claimed is:

1. A positive airway pressure device comprising:

a tube including an inner end hole and an outer end hole intercommunicating with the inner end hole, with the outer end hole being smaller than the inner end hole, with the tube adapted to be inserted into a nasal cavity; and a two-way valve located in the tube, with the two-way valve moving axially between the inner end hole and the outer end hole;

wherein the two-way valve includes a first end face and a second end face opposite to each other, the first end face being adjacent to the inner end hole, and the second end face being adjacent to the outer end hole, wherein the two-way valve further includes a fluid passage, which is a through hole extending through the first end face and the second end face to intercommunicate the inner end hole and the outer end hole.

2. The positive airway pressure device as claimed in claim 1, wherein the tube includes a tube body and a base, the tube body is coupled to the base, the inner end hole is located in the tube body, and the outer end hole is located in the base.

3. The positive airway pressure device as claimed in claim 2, wherein the base and the tube body together form a receiving space, the receiving space is located between the inner end hole and the outer end hole, and the two-way valve is located in the receiving space.

4. The positive airway pressure device as claimed in claim 2, wherein the tube body includes a coupling protrusion, the base includes a recessed portion, and the coupling portion is coupled in the recessed portion.

5. The positive airway pressure device as claimed in claim 1, wherein an outer diameter of the two-way valve is greater than a hole diameter of the inner end hole and a hole diameter of the outer end hole.

6. The positive airway pressure device as claimed in claim 1, wherein the two-way valve includes at least one first groove, and the at least one first groove intercommunicates with the inner end hole.

7. The positive airway pressure device as claimed in claim 6, wherein the at least one first groove is located on the first end face, and the at least one first groove extends along an outer wall of the two-way valve in a direction towards the second end face.

8. The positive airway pressure device as claimed in claim 1, wherein the tube includes at least one second groove, and the at least one second groove intercommunicates with the inner end hole.

9. The positive airway pressure device as claimed in claim 1, further comprising a film, with the film coupled to an outer peripheral wall of the tube.

10. The positive airway pressure device as claimed in claim 9, wherein the film is made of polyurethane material.

* * * * *